(12) United States Patent
Olah et al.

(10) Patent No.: US 7,846,978 B2
(45) Date of Patent: *Dec. 7, 2010

(54) SELECTIVE OXIDATIVE CONVERSION OF METHANE TO METHANOL, DIMETHYL ETHER AND DERIVED PRODUCTS

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/710,907

(22) Filed: Feb. 23, 2010

(65) Prior Publication Data

US 2010/0152474 A1    Jun. 17, 2010

Related U.S. Application Data

(63) Continuation of application No. 11/402,051, filed on Apr. 12, 2006, now Pat. No. 7,705,059.

(60) Provisional application No. 60/671,650, filed on Apr. 15, 2005, provisional application No. 60/763,678, filed on Jan. 30, 2006.

(51) Int. Cl.
  *C07C 27/00* (2006.01)
(52) U.S. Cl. .................... 518/700; 518/713; 518/714
(58) Field of Classification Search ............... 518/700, 518/713, 714
See application file for complete search history.

(56) References Cited

U.S. PATENT DOCUMENTS

| 4,243,613 A | 1/1981 | Brockhaus et al. ........... 568/482 |
| 5,364,887 A | 11/1994 | Konig et al. ................. 518/713 |
| 2004/0038811 A1 | 2/2004 | Parmaliana et al. ......... 502/232 |

FOREIGN PATENT DOCUMENTS

| CA | 1096884 A | 3/1991 |
| FR | 2 543 946 A1 | 10/1984 |
| JP | 58-092630 A | 6/1983 |
| JP | 59-216839 A | 12/1984 |
| WO | WO 2005/037746 A1 | 4/2005 |

OTHER PUBLICATIONS

Barbero et al., "Breakthrough in the direct conversion of methane into $c_1$-oxygenates," Chem. Commun., 1184-1185 (2001).
Larkin et al., "The direct partial oxidation of methane to organic oxygenates using a dielectric barrier discharge reactor as a catalytic reactor analog," Catalysis Today 71: 199-210 (2001).
Zang et al., "Comparative studies on direct conversion of methane to methanol/formaldehyde over La—Co—O and $ZrO_2$ supported molybdenum oxide catalysts," Topics in Catalysis 32(3-4): 215-223 (2005).
International Search Report, Application No. PCT/US2006/013743, Aug. 4, 2006.

*Primary Examiner*—Jafar Parsa
(74) *Attorney, Agent, or Firm*—Winston & Strawn LLP (57) ABSTRACT

The present invention relates to a method of producing methanol from a methane source by oxidizing methane under conditions sufficient to a mixture of methanol and formaldehyde while minimizing the formation of formic acid and carbon dioxide. The oxidation step is followed by treatment step in which formaldehyde is converted into methanol and formic acid which itself can further be converted into methanol via catalytic hydrogenation of intermediately formed methyl formate.

16 Claims, 2 Drawing Sheets

SELECTIVE OXIDATIVE CONVERSION OF METHANE TO METHANOL, DIMETHYL ETHER AND DERIVED PRODUCTS

This application is a continuation of application Ser. No. 11/402,051 filed Apr. 12, 2006, now U.S. Pat. No. 7,705,059 which application claims the benefit of provisional applications 60/671,650 filed Apr. 15, 2005 and 60/763,678 filed Jan. 30, 2006. The content of each application is expressly incorporated herein by reference thereto.

BACKGROUND

Hydrocarbons are essential in modern life. Hydrocarbons are used as fuel and raw material in various fields, including the chemical, petrochemical, plastics, and rubber industries. Fossil fuels, such as coal, oil and gas, are composed of hydrocarbons with varying ratios of carbon and hydrogen, and is non-renewably used when combusted, forming carbon dioxide and water. Despite their wide application and high demand, fossil fuels present a number of disadvantages, including the finite reserve, irreversible combustion and contribution to air pollution and global warming. Considering these disadvantages, and the increasing demand for energy, alternative sources of energy are needed.

One such alternative frequently mentioned is hydrogen, and the so-called "hydrogen economy." Hydrogen is beneficial as a clean fuel, producing only water when combusted. Free hydrogen, however, is not a natural energy source, and its generation from hydrocarbons or water is a highly energy-consuming process. Further, when hydrogen is produced from hydrocarbons, any claimed benefit of hydrogen as a clean fuel is outweighed by the fact that generation of hydrogen itself, mainly by reforming of natural gas, oil or coal to synthesis gas ("syn-gas") a mixture of CO and $H_2$, is far from clean. It consumes fossil fuels, with a quarter of the energy of the fuel being lost as heat. Hydrogen is also not a convenient energy storage medium because it is difficult and costly to handle, store, transport and distribute. As it is extremely volatile and potentially explosive, hydrogen gas requires high-pressure equipment, costly and non-existent infrastructure, special materials to minimize diffusion and leakage, and extensive safety precautions to prevent explosions.

It was suggested that a more practical alternative is methanol. Methanol, $CH_3OH$, is the simplest liquid oxygenated hydrocarbon, differing from methane ($CH_4$) by a single additional oxygen atom. Methanol, also called methyl alcohol or wood alcohol, is a colorless, water-soluble liquid with a mild alcoholic odor, and is easy to store and transport. It freezes at −97.6° C., boils at 64.6° C., and has a density of 0.791 at 20° C.

Methanol is not only a convenient and safe way to store energy, but, together with its derived dimethyl ether (DME), is an excellent fuel. Dimethyl ether is easily obtained from methanol by dehydration and is an effective fuel particularly in diesel engines because of its high cetane number and favorable properties. Methanol and dimethyl ether can be blended with gasoline or diesel and used as fuels, for example in internal combustion engines or electricity generators. One of the most efficient use of methanol is in fuel cells, particularly in direct methanol fuel cell (DMFC), in which methanol is directly oxidized with air to carbon dioxide and water while producing electricity.

Contrary to gasoline, which is a complex mixture of many different hydrocarbons and additives, methanol is a single chemical compound. It contains about half the energy density of gasoline, meaning that two liters of methanol provides the same energy as a liter of gasoline. Even though methanol's energy content is lower, it has a higher octane rating of 100 (average of the research octane number (RON) of 107 and motor octane number (MON) of 92), which means that the fuel/air mixture can be compressed to a smaller volume before being ignited. This allows the engine to run at a higher compression ratio (10-11 to 1 against 8-9 to 1 of a gasoline engine), more efficiently than a gasoline-powered engine. Efficiency is also increased by methanol's higher "flame speed," which enables faster, more complete fuel combustion in the engines. These factors explain the high efficiency of methanol despite its lower energy density than gasoline. Further, to render methanol more ignitable even under the most frigid conditions, methanol can be mixed with gasoline, with volatile compounds (e.g., dimethyl ether), with other components or with a device to vaporize or atomize methanol. For example, an automotive fuel can be prepared by adding methanol to gasoline with the fuel having a minimum gasoline content of at least 15% by volume (M85 fuel) so that it can readily start even in low temperature environments. Of course, any replacement of gasoline in such fuels will conserve oil resources, and the amount of methanol to add can be determined depending upon the specific engine design.

Methanol has a latent heat of vaporization of about 3.7 times higher than gasoline, and can absorb a significantly larger amount of heat when passing from liquid to gas state. This helps remove heat away from the engine and enables the use of an air-cooled radiator instead of a heavier water-cooled system. Thus, compared to a gasoline-powered car, a methanol-powered engine provides a smaller, lighter engine block, reduced cooling requirements, and better acceleration and mileage capabilities. Methanol is also more environment-friendly than gasoline, and produces low overall emissions of air pollutants such as hydrocarbons, $NO_x$, $SO_2$ and particulates.

Methanol is also one of the safest fuels available. Compared to gasoline, methanol's physical and chemical properties significantly reduce the risk of fire. Methanol has lower volatility, and methanol vapor must be four times more concentrated than gasoline for ignition to occur. Even when ignited, methanol burns about four times slower than gasoline, releases heat only at one-eighth the rate of gasoline fire, and is far less likely to spread to surrounding ignitable materials because of the low radiant heat output. It has been estimated by the EPA that switching from gasoline to methanol would reduce incidence of fuel-related fire by 90%. Methanol burns with a colorless flame, but additives can solve this problem.

Methanol also provides an attractive and more environment-friendly alternative to diesel fuel. Methanol does not produce smoke, soot, or particulates when combusted, in contrast to diesel fuel, which generally produces polluting particles during combustion. Methanol also produces very low emissions of NOx because it burns at a lower temperature than diesel. Furthermore, methanol has a significantly higher vapor pressure compared to diesel fuel, and the higher volatility allows easy start even in cold weather, without producing white smoke typical of cold start with a conventional diesel engine. If desired, additives or ignition improvers, such as octyl nitrate, tetrahydrofurfuryl nitrate, peroxides or higher alkyl ethers, can be added to bring methanol's cetane rating to the level closer to diesel. Methanol can also be used in the manufacture of biodiesel fuels by esterification of fatty acids.

Closely related and derived from methanol, and also a desirable alternative fuel is dimethyl ether. Dimethyl ether (DME, $CH_3OCH_3$), the simplest of all ethers, is a colorless, nontoxic, non-corrosive, non-carcinogenic and environmentally friendly chemical that is mainly used today as an aerosol propellant in spray cans, in place of the banned CFC gases. DME has a boiling point of −25° C., and is a gas under ambient conditions. DME is, however, easily handled as liquid and stored in pressurized tanks, much like liquefied petroleum gas (LPG). The interest in dimethyl ether as alternative fuel lies in its high cetane rating of 55 to 60, which is much higher than that of methanol and is also higher than the cetane rating of 40 to 55 of conventional diesel fuels. The cetane rating indicates that DME can be effectively used in diesel engines. Advantageously, DME, like methanol, is clean burning, and produces no soot particulates, black smoke or $SO_2$, and only very low amounts of $NO_x$ and other emissions even without after-treatment of its exhaust gas. Some of the physical and chemical properties DME, in comparison to diesel fuel, are shown in Table 1.

TABLE 1

Comparison of the physical properties of DME and diesel fuel

| | DME | Diesel fuel |
|---|---|---|
| Boiling point ° C. | −24.9 | 180-360 |
| Vapor pressure at 20° C. (bar) | 5.1 | — |
| Liquid density at 20° C. (kg/m³) | 668 | 840-890 |
| Heating value (kcal/kg) | 6,880 | 10,150 |
| Cetane number | 55-60 | 40-55 |
| Autoignition temperature (° C.) | 235 | 200-300 |
| Flammability limits in air (vol %) | 3.4-17 | 0.6-6.5 |

Currently, DME is exclusively produced by dehydration of methanol. A method for synthesizing DME directly from synthesis gas by combining the methanol synthesis and dehydration steps in a single process has also been developed.

Another methanol derivative is dimethyl carbonate (DMC), which can be obtained by converting methanol with phosgene or by oxidative carbonylation of the methanol. DMC has a high cetane rating, and can be blended into diesel fuel in a concentration up to 10%, reducing fuel viscosity and improving emissions.

Methanol and its derivatives, e.g., DME, DMC, and biodiesel, have many existing and potential uses. They can be used, for example, as a substitute for gasoline and diesel fuel in ICE-powered cars with only minor modifications to the existing engines and fuel systems. Methanol can also be used in fuel cells, for fuel cell vehicles (FCVs), which are considered to be the best alternative to ICEs in the transportation field. DME is also a potential substitute for LNG and LPG for heating homes and in industrial uses.

Methanol is also useful in reforming to hydrogen. In an effort to address the problems associated with hydrogen storage and distribution, suggestions have been made to use liquids rich in hydrogen such as gasoline or methanol as a source of hydrogen in vehicles via an on-board reformer. It is also considered that methanol is the safest of all materials available for such hydrogen production. Further, because of the high hydrogen content of liquid methanol, even compared to pure cryogenic hydrogen (98.8 g of hydrogen in a liter of methanol at room temperature compared to 70.8 g in liquid hydrogen at −253° C.), methanol is an excellent carrier of hydrogen fuel. The absence of C—C bonds in methanol, which are difficult to break, facilitates its transformation to pure hydrogen in 80 to 90% efficiency.

In contrast to a pure hydrogen-based storage system, a reformer system is compact, containing on a volume basis more hydrogen than even liquid hydrogen, and is easy to store and handle without pressurization. A methanol steam reformer is also advantageous in allowing operation at a much lower temperature (250-350° C.) and for being better adapted to on-board applications. Furthermore, methanol contains no sulfur, a contaminant for fuel cells, and no nitrogen oxides are formed from a methanol reformer because of the low operating temperature. Particulate matter and $NO_x$ emissions are virtually eliminated, and other emissions are minimal. Moreover, methanol allows refueling to be as quick and easy as with diesel fuel. Thus, an on-board methanol reformer enables rapid and efficient delivery of hydrogen from liquid fuel that can be easily distributed and stored in the vehicle. To date, methanol is the only liquid fuel that has been processed and demonstrated on a practical scale as suitable for use in a fuel cell for transportation applications.

In addition to on-board reforming, methanol also enables convenient production of hydrogen in fueling stations for refueling hydrogen fuel cell vehicles. A fuel cell, an electrochemical device that converts free chemical energy of fuel directly into electrical energy, provides a highly efficient way of producing electricity via catalytic electrochemical oxidation. For example, hydrogen and oxygen (air) are combined in an electrochemical cell-like device to produce water and electricity. The process is clean, with water being the only byproduct. However, because hydrogen itself must first be produced in an energy-consuming process, by electrolysis or from a hydrocarbon source (fossil fuel) with a reformer, hydrogen fuel cells are still necessarily limited in utility.

A system for producing high purity hydrogen has been developed by steam reforming of methanol with a highly active catalyst, which allows operation at a relatively low temperature (240-290° C.) and enables flexibility in operation as well as rapid start-up and stop. These methanol-to-hydrogen (MTH) units, ranging in production capacity from 50 to 4000 m³$H_2$ per hour, are already used in various industries, including the electronic, glass, ceramic, and food processing industries, and provide excellent reliability, prolonged life span, and minimal maintenance. Operating at a relatively low temperature, the MTH process has a clear advantage over reforming of natural gas and other hydrocarbons which must be conducted at above 600° C., because less energy is needed to heat methanol to the appropriate reaction temperature.

The usefulness of methanol has led to development of other reforming processes, for example, a process known as oxidative steam reforming, which combines steam reforming, partial oxidation of methanol, and novel catalyst systems. Oxidative steam reforming produces high purity hydrogen with zero or trace amounts of CO, at high methanol conversion and temperatures as low as 230° C. It has the advantage of being, contrary to steam reforming, an exothermic reaction, therefore minimizing energy consumption. There is also autothermal reforming of methanol, which combines steam reforming and partial oxidation of methanol in a specific ratio and addresses any drawback of an exothermic reaction by producing only enough energy to sustain itself. Autothermal reforming is neither exothermic nor endothermic, and does not require any external heating once the reaction temperature is reached. Despite the aforementioned possibilities, hydrogen fuel cells must use highly volatile and flammable hydrogen or reformer systems.

U.S. Pat. No. 5,599,638 discloses a simple direct methanol fuel cell (DMFC) to address the disadvantages of hydrogen fuel cells. In contrast to a hydrogen fuel cell, the DMFC is not dependent on generation of hydrogen by processes such as electrolysis of water or reformation of natural gas or hydrocarbon. The DMFC is also more cost effective because methanol, as a liquid fuel, does not require cooling at ambient temperatures or costly high pressure infrastructure and can be used with existing storage and dispensing units, unlike hydrogen fuel, whose storage and distribution requires new infrastructure. Further, methanol has a relatively high theoretical volumetric energy density compared to other systems such as conventional batteries and the $H_2$-PEM fuel cell. This is of great importance for small portable applications (cellular phones, laptop computers, etc.), for which small size and weight of energy unit is desired.

The DMFC offers numerous benefits in various areas, including the transportation sector. By eliminating the need for a methanol steam reformer, the DMFC significantly reduces the cost, complexity and weight of the vehicle, and improves fuel economy. A DMFC system is also comparable in its simplicity to a direct hydrogen fuel cell, without the cumbersome problems of on-board hydrogen storage or hydrogen producing reformers. Because only water and $CO_2$ are emitted, emissions of other pollutants (e.g., $NO_x$, PM, $SO_2$, etc.) are eliminated. Direct methanol fuel cell vehicles are expected to be virtually zero emission vehicles (ZEV), and use of methanol fuel cell vehicles offers to nearly eliminate air pollutants from vehicles in the long term. Further, unlike ICE vehicles, the emission profile is expected to remain nearly unchanged over time. New membranes based on hydrocarbon or hydrofluorocarbon materials with reduced cost and crossover characteristics have been developed that allow room temperature efficiency of 34%.

Methanol as indicated provides a number of important advantages as transportation fuel. Contrary to hydrogen, methanol does not require any energy intensive procedures for pressurization or liquefaction. Because it is a liquid at room temperature, it can be easily handled, stored, distributed and carried in vehicles. It can act as an ideal hydrogen carrier for fuel cell vehicles through on-board methanol reformers, and can be used directly in DMFC vehicles.

Methanol is also an attractive source of fuel for static applications. For example, methanol can be used directly as fuel in gas turbines to generate electric power. Gas turbines typically use natural gas or light petroleum distillate fractions as fuel. Compared to such fuels, methanol can achieve higher power output and lower $NO_x$ emissions because of its lower flame temperature. Since methanol does not contain sulfur, $SO_2$ emissions are also eliminated. Operation on methanol offers the same flexibility as on natural gas and distillate fuels, and can be performed with existing turbines, originally designed for natural gas or other fossil fuels, after relatively easy modification. Methanol is also an attractive fuel since fuel-grade methanol, with lower production cost than higher purity chemical-grade methanol, can be used in turbines. Because the size and weight of a fuel cell is of less importance in static applications than mobile applications, various fuel cells other than PEM fuel cells and DMFC, such as phosphoric acid, molten carbonate and solid oxide fuel cells (PAFC, MCFC, and SOFC, respectively), can also be used.

Figure 1:
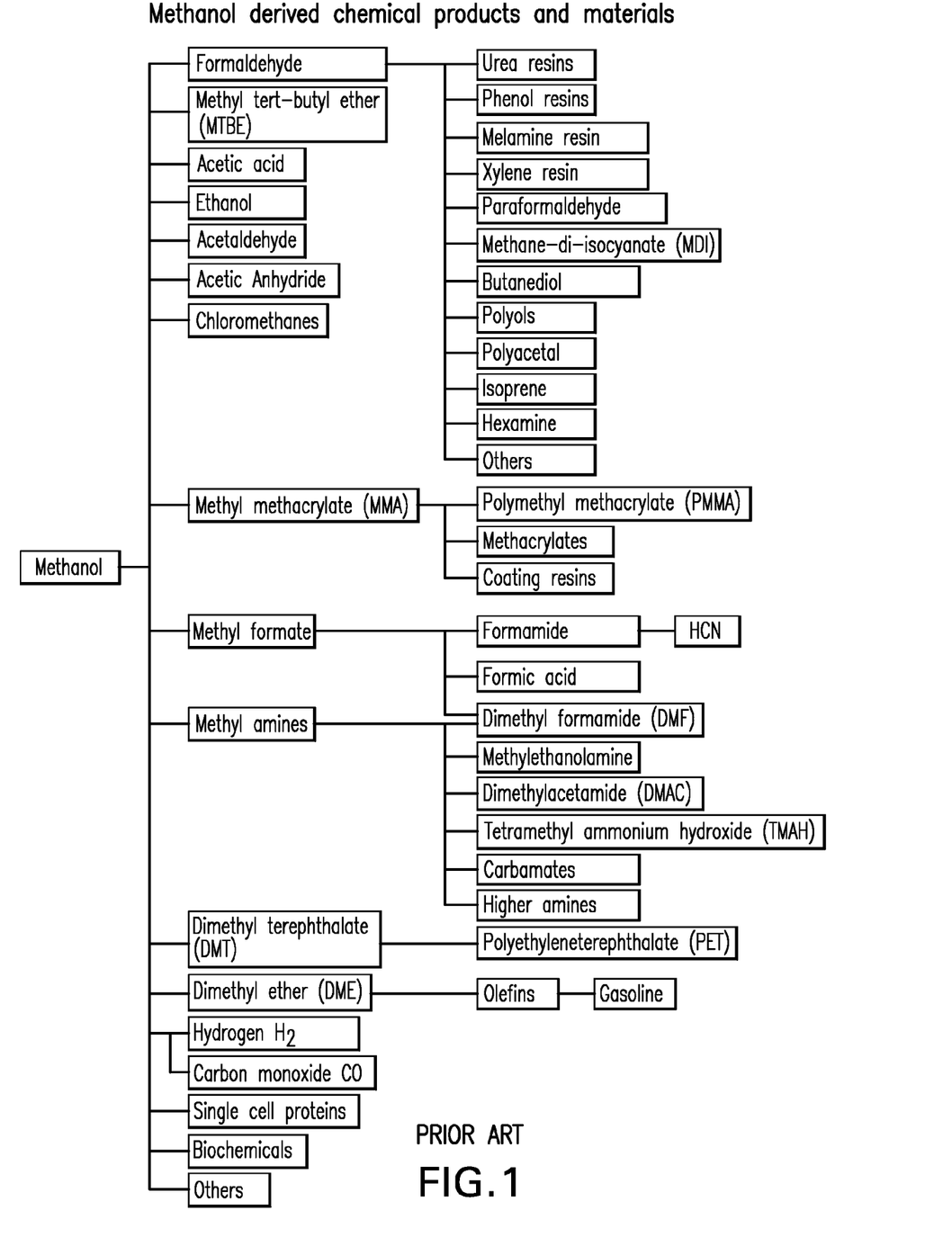
FIG. 1 shows known examples of methanol-derived chemical products and materials.

In addition to use as fuels, methanol and methanol-derived chemicals have other significant applications in the chemical industry. Today, methanol is one of the most important feedstock in the chemical industry. Most of the 32 million tons of annually produced methanol is used to manufacture a large variety of chemical products and materials, including basic chemicals such as formaldehyde, acetic acid, MTBE (although it is increasingly phased out for environmental reasons), as well as various polymers, paints, adhesives, construction materials, and others. Worldwide, almost 70% of methanol is used to produce formaldehyde (38%), methyl-tert-butyl ether (MTBE, 20%) and acetic acid (11%). Methanol is also a feedstock for chloromethanes, methylamines, methyl methacrylate, and dimethyl terephthalate, among others. These chemical intermediates are then processed to manufacture products such as paints, resins, silicones, adhesives, antifreeze, and plastics. Formaldehyde, produced in large quantities from methanol, is mainly used to prepare phenol-, urea- and melamine-formaldehyde and polyacetal resins as well as butanediol and methylene bis(4-phenyl isocyanate) (MDI; MDI foam is used as insulation in refrigerators, doors, and in car dashboards and bumpers). Formaldehyde resins are predominantly employed as an adhesive in a wide variety of applications, e.g., manufacture of particle boards, plywood and other wood panels. Examples of methanol-derived chemical products and materials are shown in FIG. 1.

In producing basic chemicals, raw material feedstock constitutes typically up to 60-70% of the manufacturing costs. The cost of feedstock therefore plays a significant economic role. Because of its lower cost, methanol is considered a potential feedstock for processes currently utilizing more expensive feedstocks such as ethylene and propylene, to produce chemicals including acetic acid, acetaldehyde, ethanol, ethylene glycol, styrene, and ethylbenzene, and various synthetic hydrocarbon products. For example, direct conversion of methanol to ethanol can be achieved using a rhodium-based catalyst, which has been found to promote the reductive carbonylation of methanol to acetaldehyde with selectivity close to 90%, and a ruthenium catalyst, which further reduces acetaldehyde to ethanol. The possibility of producing ethylene glycol via methanol oxidative coupling instead of the usual process using ethylene as feedstock is also pursued, and significant advances for synthesizing ethylene glycol from dimethyl ether, obtained by methanol dehydration, have also been made.

Conversion of methanol to olefins such as ethylene and propylene, also known as methanol to olefin (MTO) technology, is particularly promising considering the high demand for olefin materials, especially in polyolefin production. The MTO technology is presently a two-step process, in which natural gas is converted to methanol via syn-gas and methanol is then transformed to olefin. It is considered that methanol is first dehydrated to dimethyl ether (DME), which then reacts to form ethylene and/or propylene. Small amounts of butenes, higher olefins, alkanes, and aromatics are also formed.

Various catalysts, e.g., synthetic aluminosilicate zeolite catalysts, such as ZSM-5 (a zeolite developed by Mobil), silicoaluminophosphate (SAPO) molecular sieves such as SAPO-34 and SAPO-17 (UOP), as well as bi-functional supported acid-base catalysts such as tungsten oxide over alumina ($WO_3/Al_2O_3$), have been found to be active in converting methanol to ethylene and propylene at a temperature between 250 and 350° C. The type and amount of the end product depend on the type of the catalyst and the MTO process used. Depending on the operating conditions, the weight ratio of propylene to ethylene can be modified between about 0.77 and 1.33, allowing considerable flexibility. For example, when using SAPO-34 according to an MTO process developed by UOP and Norsk Hydro, methanol is converted to ethylene and propylene at more than 80% selectivity, and also to butene, a valuable starting material for a number of products, at about 10%. When using an MTO process developed by Lurgi with ZSM-5 catalysts, mostly propylene is produced at yields above 70%. A process developed by ExxonMobil, with ZSM-5 catalyst, produces hydrocarbons in the gasoline and/or distillate range at selectivity greater than 95%.

There is also a methanol to gasoline (MTG) process, in which medium-pore zeolites with considerable acidity, e.g., ZSM-5, are used as catalysts. In this process, methanol is first dehydrated to an equilibrium mixture of dimethyl ether, methanol and water over a catalyst, and this mixture is then converted to light olefins, primarily ethylene and propylene. The light olefins can undergo further transformations to higher olefins, $C_3$-$C_6$ alkanes, and $C_6$-$C_{10}$ aromatics such as toluene, xylenes, and trimethylbenzene.

With decreasing oil and gas reserves, it is inevitable that synthetic hydrocarbons would play a major role. Thus, methanol-based synthetic hydrocarbons and chemicals available through MTG and MTO processes will assume increasing importance in replacing oil and gas-based materials. The listed uses of methanol is only illustrative and not limiting.

Methanol can also be used as a source of single cell proteins. A single cell protein (SCP) refers to a protein produced by a microorganism which degrades hydrocarbon substrates while gaining energy. The protein content depends on the type of microorganism, e.g., bacteria, yeast, mold, etc. The SCP has many uses, including uses as food and animal feed.

Considering the numerous uses of methanol, it is clearly desirable to have improved and efficient methods of producing methanol. Currently, methanol is almost exclusively made from synthesis gas obtained from incomplete combustion (or catalytic reforming) of fossil fuel, mainly natural gas (methane) and coal.

Methanol can also be made from renewable biomass, but such methanol production also involves syn-gas and may not be energetically favorable and limited in terms of scale. As used herein, the term "biomass" includes any type of plant or animal material, i.e., materials produced by a life form, including wood and wood wastes, agricultural crops and their waste byproducts, municipal solid waste, animal waste, aquatic plants, and algae. The method of transforming biomass to methanol is similar to the method of producing methanol from coal, and requires gasification of biomass to syn-gas, followed by methanol synthesis by the same processes used with fossil fuel. Use of biomass also presents other disadvantages, such as low energy density and high cost of collecting and transporting bulky biomass. Although recent improvements involving the use of "biocrude," black liquid obtained from fast pyrolysis of biomass, is somewhat promising, more development is needed for commercial application of biocrude.

The presently existing method of producing methanol involves syn-gas. Syn-gas is a mixture of hydrogen, carbon monoxide and carbon dioxide, and produces methanol over a heterogeneous catalyst according to the following equations:

The first two reactions are exothermic with heat of reaction equal to −21.7 kcal·mol$^{-1}$ and −9.8 kcal·mol$^{-1}$, respectively, and result in a decrease in volume. Conversion to methanol is favored by increasing the pressure and decreasing the temperature according to Le Chatelier's principle. The third equation describes the endothermic reverse water gas shift reaction (RWGSR). Carbon monoxide produced in the third reaction can further react with hydrogen to produce methanol. The second reaction is simply the sum of the first and the third reactions. Each of these reactions is reversible, and is therefore limited by thermodynamic equilibrium under the reaction conditions, e.g., temperature, pressure and composition of the syn-gas.

Synthesis gas for methanol production can be obtained by reforming or partial oxidation of any carbonaceous material, such as coal, coke, natural gas, petroleum, heavy oil, and asphalt. The composition of syn-gas is generally characterized by the stoichiometric number S, corresponding to the equation shown below.

$$S = \frac{(\text{moles } H_2 - \text{moles } CO_2)}{(\text{moles } CO + \text{moles } CO_2)}$$

Ideally, S should be equal to or slightly above 2. A value above 2 indicates excess hydrogen, while a value below 2 indicates relative hydrogen deficiency. Reforming of feedstock having a higher H/C ratio, such as propane, butane or naphthas, leads to S values in the vicinity of 2, ideal for conversion to methanol. When coal or methane is used, however, additional treatment is required to obtain an optimal S value. Synthesis gas from coal requires treatment to avoid formation of undesired byproducts. Steam reforming of methane yields syn-gas with a stoichiometric number of 2.8 to 3.0, and requires lowering the S value closer to 2 by adding $CO_2$ or using excess hydrogen in some other process such as ammonia synthesis. However, natural gas is still the preferred feedstock for methanol production because it offers high hydrogen content and, additionally, the lowest energy consumption, capital investment and operating costs. Natural gas also contains fewer impurities such as sulfur, halogenated compounds, and metals which may poison the catalysts used in the process.

The existing processes invariably employ extremely active and selective copper-based catalysts, differing only in the reactor design and catalyst arrangement. Because only part of syn-gas is converted to methanol after passing over the catalyst, the remaining syn-gas is recycled after separation of methanol and water. There is also a more recently developed liquid phase process for methanol production, during which syn-gas is bubbled into liquid. Although the existing processes have methanol selectivity greater than 99% and energy efficiency above 70%, crude methanol leaving the reactor still contains water and other impurities, such as dissolved gas (e.g., methane, CO, and $CO_2$), dimethyl ether, methyl formate, acetone, higher alcohols (ethanol, propanol, butanol), and long-chain hydrocarbons. Commercially, methanol is available in three grades of purity: fuel grade, "A" grade, generally used as a solvent, and "AA" or chemical grade. Chemical grade has the highest purity with a methanol content exceeding 99.85% and is the standard generally observed in the industry for methanol production. The syn-gas generation and purification steps are critical in the existing processes, and the end result would largely depend on the nature and purity of the feedstock. To achieve the desired level of purity, methanol produced by the existing processes is usually purified by sufficient distillation. Another major disadvantage of the existing process for producing methanol through syn-gas is the energy requirement of the first highly endothermic steam reforming step. The process is also inefficient because it involves transformation of methane in an oxidative reaction to carbon monoxide (and some $CO_2$), which in turn must be reduced to methanol.

The selective conversion of methane (natural gas) to methanol without first producing a mixture of carbon monoxide and hydrogen (syn-gas) is a long standing challenge and a much desired practical goal. Although various C—H activations of converting methane to methyl derivatives have been reported, such chemistry is still far from being practical. Whereas claims of selective and direct oxidation of methane to methanol were made using a variety of oxidizing agents and metal oxide catalysts, any claimed high selectivity conversion was achieved only in very low yields of methanol. At higher conversions, selectivity is rapidly lost and only mixtures of oxidation products (formaldehyde, formic acid and carbon dioxide) are obtained.

Thus, although various, detailed reaction conditions have been explored to achieve high methanol conversion rate without complete oxidation, it has not yet been possible to achieve the combination of high yield, selectivity and catalyst stability that would render direct oxidative conversion competitive with the conventional syn-gas-based methanol production. There is a need for improved processes that effectively produce methanol from methane by high selectivity good yield oxidative conversion, and these are now provided by the present invention.

SUMMARY OF THE INVENTION

The invention relates to a method of preparing methanol from a methane source without first producing syn-gas. This method comprises oxidizing methane under conditions sufficient to produce a mixture of methanol and formaldehyde with smaller amounts of formic acid and carbon dioxide; converting the formaldehyde under conditions sufficient to form methanol and formic acid or methyl formate; and subsequently hydrogenatively converting the methyl formate under conditions sufficient to form methanol. Advantageously, the methanol oxidation mixture is treated without separation of its components to convert substantially all the formaldehyde therein to methyl alcohol without any by-products. Preferably, unreacted methane is recovered and recycled to the oxidizing step.

The formaldehyde can be converted via solid base catalysis into methanol and formic acid, which are then subsequently converted under conditions sufficient to form methyl formate. The formic acid can be reacted with the formaldehyde under conditions sufficient to produce methanol. It is also possible to subject the formaldehyde to catalytic dimerization under conditions sufficient to form methyl formate which then is converted to methanol. The methyl formate can be converted to methanol by catalytic hydrogenation, or by electrochemical reduction.

The methane source may be natural gas, coal gas, or a methane hydrate. The methane source may be oxidized by contact with an oxidizing agent under conditions sufficient to substantially form methanol and formaldehyde. Useful oxidizing agents include molecular oxygen or air and a suitable catalyst, or hydrogen peroxide and an oxide catalyst. The oxide catalyst may be a single or mixed catalyst based on V, Ti, Ga, Mg, Cu, Mo, Bi, Fe, Mn, Co, Nb, Zr, La or Sn and that is optionally provided on a silica or alumina support.

To form other products, the methanol can be dehydrated under conditions sufficient to produce dimethyl ether. The dimethyl ether can be heated in the presence of an acidic-basic or zeolitic catalysts to form ethylene or propylene. The latter can be converted either to higher olefins, synthetic hydrocarbons or aromatics and their products for use as feedstocks for chemicals or as transportation fuels. Ethanol or propanol can be prepared by hydration of the ethylene or propylene, respectively. Alternatively, the dimethyl ether can be used as a substitute for natural gas and LPG for heating purposes for households or industrial use.

In the area of synthetic fuels, an improved diesel fuel can be prepared by mixing sufficient amounts of dimethyl ether with conventional diesel fuel. Also, dimethyl carbonate can be formed by reaction of the methanol with phosgene or by the oxidative carbonylation of the methanol, and an improved diesel fuel can be prepared by mixing sufficient amounts of dimethyl carbonate with conventional diesel fuel. A transportation fuel can be prepared by adding methanol to gasoline with the fuel having a minimum gasoline content of at least 15% by volume.

As to other uses, the methanol or dimethyl ether can act as convenient energy storage and transportation materials in order to minimize or eliminate the disadvantages or dangers inherent in the use and transportation of LNG or LPG. It is also possible to use the methanol for preparing single cell proteins for human or animal alimentation.

BRIEF DESCRIPTION OF THE DRAWINGS

The features and benefits of the invention will become more evident from review of the following detailed description of illustrative embodiments and the accompanying drawings, wherein.

DETAILED DESCRIPTION OF THE PREFERRED EMBODIMENTS

The invention relates to new, efficient, oxidative conversions of a methane source such as natural gas to methanol or dimethyl ether. This method comprises oxidizing methane under conditions sufficient to obtain a mixture of methanol and formaldehyde, but substantially excluding formic acid and carbon dioxide. Formaldehyde is subsequently converted under conditions sufficient to form methanol and formic acid or methyl formate; and subsequently the methyl formate is hydrogenatively converted under conditions sufficient to form methanol without any by-products. Preferably, the methane oxidation mixture is treated directly without separation of its components to produce methanol. This process achieves high selectivity in methanol with practically applicable yields.

In one embodiment, the formaldehyde formed in the methane oxidation step is catalytically converted via a modified Cannizzarro reaction to methanol and formic acid, which are subsequently reacted under conditions sufficient to form methyl formate. Alternatively, the formaldehyde is converted to methyl formate by its catalytic dimerization. Methyl formate by itself has a high octane number of 115 (RON) and can serve as a fuel for internal combustion engines. In another embodiment, the formic acid that is obtained is used to reduce formaldehyde to produce methanol.

Advantageously, methane available from any of its natural sources (natural gas, coal field methane, methane hydrates, etc.) is oxidized by contact with an oxidizing agent. The oxidizing agent may be molecular oxygen, or can comprise hydrogen peroxide and an oxide catalyst. The oxide (mixed oxide) catalysts may be based on V, Ti, Ga, Mg, Cu, Mo, Bi, Fe, Mn, Co, Nb, Zr, La or Sn and is optionally provided on a silica or alumina support. Any unreacted methane may be recovered and then recycled to the oxidizing step.

Methyl formate can be converted without any by-product to methanol by its catalytic hydrogenation or by electrochemical reduction. If desired, methanol can subsequently be dehydrated under conditions sufficient to produce dimethyl ether.

The resulting methanol product can be used in a variety of ways. It is a convenient and safe material for energy storage and transportation. It is an excellent fuel for internal combustion engines and fuel cells. Methanol can be dehydrated under conditions sufficient to produce dimethyl ether. Dimethyl ether is an excellent substitute for diesel fuel. Methanol and/or dimethyl ether can be catalytically converted to ethylene or propylene (as well as other olefins). These light olefins can be converted into synthetic hydrocarbon mixtures and their products including for example ethanol (by hydration of ethylene), higher carbon olefins or aromatics and be used as feedstock for derived varied chemicals and transportation fuels. Methanol is also useful as a source of single cell proteins.

The invention relates to new, efficient, oxidative conversions of a methane source such as natural gas to methanol or dimethyl ether. This method comprises oxidizing methane under conditions sufficient to obtain a mixture of methanol and formaldehyde, but substantially excluding formic acid and carbon dioxide. Formaldehyde is subsequently converted under conditions sufficient to form methanol and formic acid or methyl formate; and subsequently the methyl formate is hydrogenatively converted under conditions sufficient to form methanol without any by-products. Preferably, the methane oxidation mixture is treated directly without separation of its components to produce methanol. This process achieves high selectivity in methanol with practically applicable yields.

In one embodiment, the formaldehyde formed in the methane oxidation step is catalytically converted via a modified Cannizarro reaction to methanol and formic acid, which are subsequently reacted under conditions sufficient to form methyl formate. Alternatively, the formaldehyde is converted to methyl formate by its catalytic dimerization. Methyl formate by itself has a high octane number of 115 (RON) and can serve as a fuel for internal combustion engines. In another embodiment, the formic acid that is obtained is used to reduce formaldehyde to produce methanol.

Advantageously, methane available from any of its natural sources (natural gas, coal field methane, methane hydrates, etc.) is oxidized by contact with an oxidizing agent. The oxidizing agent may be molecular oxygen, or can comprise hydrogen peroxide and an oxide catalyst. The oxide (mixed oxide) catalysts may be based on V, Ti, Ga, Mg, Cu, Mo, Bi, Fe, Mn, Co, Nb, Zr, La or Sn and is optionally provided on a silica or alumina support. Any unreacted methane may be recovered and then recycled to the oxidizing step.

Methyl formate can be converted without any by-product to methanol by its catalytic hydrogenation or by electrochemical reduction. If desired, methanol can subsequently be dehydrated under conditions sufficient to produce dimethyl ether.

The resulting methanol product can be used in a variety of ways. It is a convenient and safe material for energy storage and transportation. It is an excellent fuel for internal combustion engines and fuel cells. Methanol can be dehydrated under conditions sufficient to produce dimethyl ether. Dimethyl ether is an excellent substitute for diesel fuel. Methanol and/or dimethyl ether can be catalytically converted to ethylene or propylene (as well as other olefins). These light olefins can be converted into synthetic hydrocarbon mixtures and their products including for example ethanol (by hydration of ethylene), higher carbon olefins or aromatics and be used as feedstock for derived varied chemicals and transportation fuels. Methanol is also useful as a source of single cell proteins.

The invention relates to a method of synthesizing methanol by oxidative conversion of methane (natural gas) which avoids initial production of syn-gas. It has now been discovered that methane can be selectively, and at the same time with high conversion, converted to methanol by using an initial oxidation step, which produces a mixture of methanol with formaldehyde as the major products. This oxidation step is followed by a treatment step, during which the mixture is treated without any separation, resulting in significantly increasing the yield of methanol. This makes the overall process practical for the production of methanol without the necessity of converting methane first to syn-gas and producing methanol subsequently by presently used Fischer-Tropsch type chemistry.

The initial oxidation of methane to a mixture of methanol and formaldehyde can utilize any of the known catalytic oxidation procedures in a flow system between temperatures of about 150-700° C., with the formation of formic acid and carbon dioxide to be kept to a minimum. The skilled person is well aware of general wide and feasible conditions to conduct this oxidation in this manner. Such oxidations can utilize different oxidizing agents preferably oxygen (or air). Oxidation with hydrogen peroxide or its equivalents are also effective over a variety of catalysts. Varied oxide (mixed oxide) catalysts based on V, Ti, Ga, Mg, Cu, Mo, Bi, Fe, Mn, Co, Nb, Zr, La or Sn and the like are used preferably on supports such as silica or alumina. The overall amount of oxygenate formation in a single pass though is generally kept at less than about 20-30% with the unreacted methane being recycled.

It was reported that in the homogeneous gas phase oxidation of methane, methane is reacted with oxygen at a high pressure (about 30-200 atm) and a high temperature (about 200-500° C.). Optimum conditions for selective oxidation to methanol have been extensively investigated. It was observed that selectivity to methanol increases with decreasing oxygen concentration in the system. At best, 75-80% selectivity in methanol formation at 8-10% conversion, was achieved under cold flame conditions (450° C., 65 atm, less than 5% $O_2$ content), using a glass-lined reactor, which seemed to suppress secondary reactions. Most other studies obtained under their best reaction conditions (temperatures of 450-500° C. and pressures of 30-60 atm) reported selectivities of 30-40% methanol with 5-10% methane conversion. At high pressure, gas phase radical reactions are predominant, limiting the expected favorable effects of solid catalysts. Selectivity to methanol can only be moderately influenced by controlling the factors that affect radical reactions such as reactor design and shape and residence time of the reactants.

At about ambient pressure (1 atm), catalysts can play a crucial role in partial oxidation of methane with $O_2$. A large number of catalysts, primarily metal oxides and mixed oxides, have been studied. Metals have also been tested but they tend to favor complete oxidation. In most cases, the reactions were performed at temperatures from about 600 to 800° C., and formaldehyde (HCHO) was obtained as the predominant, and often the only, oxidation product. Silica itself exhibits a unique activity in oxidation of methane to formaldehyde. Higher methane conversions were, however, obtained with silica-supported molybdenum ($MoO_3$) and vanadium ($V_2O_5$) oxide catalysts. The yield of formaldehyde remained nevertheless in the range of 1 to 5%. An iron molybdate catalyst, $Fe_2O_3(MoO_3)_{2.25}$, was found to be the most active catalyst for partial oxidation of methane, with a reported formaldehyde yield of 23%. Reaction over a silica supported $PCl_3$—$MoCl_5$—$R_4Sn$ catalyst gave a 16% yield. A silica-supported $MoO_3$ catalyst has been observed to show a high selectivity of 90% to oxygenated compounds ($CH_3OH$ and HCHO) at methane conversion of 20-25% in excess steam. At the high temperatures used for partial oxidation of methane, methanol formed on the catalyst's surface is rapidly decomposed or oxidized to formaldehyde and/or carbon oxides, explaining its absence in the obtained product mixture.

In order to minimize formation of byproducts and increase selectivity to methanol, use of lower reaction temperatures (<250° C.) is preferable. Currently used catalysts for methane oxidation are, however, not sufficiently active at lower temperatures. Since gas phase reactions generally require higher temperatures (>400° C.), liquid phase reactions operating at more moderate temperatures can be used. For example, methanol can be obtained through electrophilic oxygenation (i.e., oxygen functionalization) of methane in superacids (Olah et. al. Angew. Chem. Int. Ed. Engl. 1978, 17, 909). When methane is reacted in superacids (Bronsted acids that are many million times stronger than concentrated sulfuric acid) at room temperature with hydrogen peroxide ($H_2O_2$), methane produces methanol in high selectivity. The reaction proceeds in strong acids through the insertion of protonated hydrogen peroxide, $H_3O_2^+$, into the methane C—H bond. The methanol formed in the strong acid system is in protonated form, $CH_3OH_2^+$, and is protected from further oxidation, resulting in the high selectivity observed. Considering the generally high cost of liquid superacids, cheaper peroxides and strong acid systems can be used.

Methanol formed from oxidation of methane can be thus chemically protected in strong acids systems inhibiting subsequent oxidation using predominantly metals and metal complex catalysts dissolved in sulfuric acid or oleums (Periana et al. Science, 1993, 259, 340). Several homogeneous catalytic systems activate under these conditions the otherwise very unreactive C—H bonds of methane at lower temperatures and with surprisingly high selectivity. At a temperature around 200° C., the conversion of methane to methanol by concentrated sulfuric acid using an $HgSO_4$ catalyst is efficient. Oxidation of methane produces methyl hydrogen sulfate ($CH_3OSO_3H$), which can be hydrolyzed to methanol in a separate step. At a conversion of 50%, 85% selectivity to methyl hydrogen sulfate is achieved. To complete the catalytic cycle, $Hg^+$ is reoxidized to $Hg^{2+}$ by $H_2SO_4$. Overall, the process uses one molecule of sulfuric acid for each molecule of methanol produced. $SO_2$ generated during the process can be easily oxidized to $SO_3$, which upon reaction with $H_2O$ will produce $H_2SO_4$ that can be recycled.

The cleavage of methyl hydrogen sulfate to methanol and its separation from sulfuric acid media is, however, an energy consuming cumbersome process requiring regeneration of sulfuric acid. The use of poisonous mercury also makes the process also somewhat unattractive. However, non-toxic metals such as platinum, iridium, rhodium, palladium, ruthenium, and gold, can also be used in methane oxidation, the best results are obtained with a platinum complex in $H_2SO_4$.

As water formed during the oxidation reaction progressively dilutes the sulfuric acid, decreasing its acidity. Because the activity of platinum, as well as those of mercury and most metal systems, decrease rapidly at lower acidity, the oxidative conversion is conducted in oleum (a mixture of $H_2SO_4$ and $SO_3$). $SO_3$ reacts with the water formed during the reaction to give $H_2SO_4$, thereby avoiding a decrease in acidity.

As methanol is formed in small mounts mostly with formaldehyde (and formic acid) in direct methane oxidation with air or oxygen, it has now been found that this mixture can be further processed in a second treatment step without prior separation, resulting in a substantial increase in methanol content and making the overall process selective and practical for commercial production of methanol. This subsequent treatment of formaldehyde and formic acid, formed in the oxidation step, can be carried out in different ways.

According to one embodiment, formaldehyde is treated over a solid base catalyst such as CaO and MgO, deposited on a suitable carrier, in a variation of the so-called Cannizarro reaction, producing methanol and formic acid. These products readily react with each other to form methyl formate.

2HCHO→$CH_3OH$+HCOOH $CH_3OH$+HCOOH→$HCOOCH_3$+$H_2O$

An alternative way to carry out the conversion of formaldehyde into methyl formate involves a modification of the Tischenko reaction, i.e., catalytic dimerization of formaldehyde with an aluminum alkoxide catalyst or with Cu, PbO, $SnO_2$—$V_2O_5$, $Fe_2O_3$—$V_2O_5$, $SnO_2$—$MoO_3$, $SnO_2$—$Sb_2O_5$ or $ZrO_2$ catalysts converting formaldehyde into methyl formate over a temperature range of about 120 to 180° C. The skilled chemist is again familiar with the general wide practical and feasible conditions for carrying out these reactions in high conversions and yields.

$$2CH_2O \xrightarrow{Al(OCH_2R)_3} HCOOCH_3$$

Methyl formate obtained via the Cannizzarro or Tischenko reaction is subsequently catalytically hydrogenated over copper chromite catalyst giving 2 moles of methanol with no byproduct. Methyl formate can also be electrochemically reduced using Cu, Sn, Pb electrodes.

$HCOOCH_3$+$H_2$→$2CH_3OH$

Thus the overall reaction is:

$$2\ CH_2O \xrightarrow{2\ H_2} 2\ CH_3OH$$

Formic acid formed in the Cannizarro type reaction can itself serve as reducing agent (as a source of hydrogen) when reacted thermally or catalytically with formaldehyde to produce methanol.

$CH_2O$+$HCO_2H$→$CH_3OH$+$CO_2$

Suitable combinations of these reactions allow oxidative conversion of methane to methanol with overall high selectivity and yield. Combining with the Cannizarro type reaction step gives two moles of methanol for three moles of formaldehyde with one mole of carbon dioxide available to be recycled to produce additional methanol according to the method described in copending U.S. patent application 11/402,050 of G. Olah et al. entitled Efficient And Selective Conversion Of Carbon Dioxide To Methanol, Dimethyl Ether And Derived Products filed of even date herewith, the entire content of which is incorporated herein by reference thereto.

As methanol is readily dehydrated to dimethyl ether, the present oxidative conversion of methane to methanol is also well suited to produce dimethyl ether for use as a fuel or in chemical applications. To the extent that any preferred reaction conditions are desired, routine testing can be conducted to find such preferred or optimized conditions.

Any suitable source of natural gas or methane can be used for methanol production according to the present invention. Other than the conventional natural gas sources, methanol can be produced, for instance, from "biogas," a result of anaerobic bacteria's breaking down organic material in the absence of oxygen. Biogas is produced in the digestive tracks of most mammals, organisms such as termites, and microorganisms during digestion, as well as in wetlands, swamps and bogs, where large amounts of rotting vegetation may accumulate. Biogas is composed mainly of methane and carbon dioxide in varying proportions, and contains trace levels of other elements such as hydrogen sulfide ($H_2S$), hydrogen, and/or carbon monoxide.

The present method of selectively converting methane to methanol is particularly advantageous in view of the numerous applications of methanol as fuel and for other chemical applications. The safety and versatility of methanol makes the present direct conversion especially desirable.

As known in the art, methanol can be blended with gasoline as an oxygenated additive and used in internal combustion engines with only minor modifications. Methanol can also be used to generate electricity in a fuel cell, by catalytically reforming methanol to $H_2$ and CO or by allowing methanol to directly react with air in a direct methanol fuel cell (DMFC). DMFC greatly simplifies the fuel cell technology and makes it readily available to a wide range of applications, including portable mobile electronic devices and electricity generators.

Another significant benefit of direct conversion of natural gas (methane) to methanol or dimethyl ether is ready and safe transportation of fuel when pipelines are not feasible or available. LNG (liquefied natural gas), which is currently widely transported across the seas under cryogenic conditions using very large tankers (>200,000 tonnes), unloaded at LNG terminals, and fed into pipelines to satisfy increasing needs and substitute for diminishing local natural gas sources, presents potential hazards for devastating accidents. The direct conversion of natural gas to methanol (dimethyl ether) according to the present invention provides a safe alternative to transporting natural gas.

In addition to being a conveniently storable energy source and fuel, methanol is also the starting material for various chemicals such as formaldehyde, acetic acid, and a number of other products including polymers, paints, adhesives, construction materials, synthetic chemicals, pharmaceuticals, and single cell proteins. Significantly, methanol can be conveniently converted in a simple catalytic step to ethylene and/or propylene (e.g., in a methanol to olefin or MTO process), the building blocks for producing synthetic hydrocarbons and their products. This means that hydrocarbon fuel and products currently derived from fossil fuel can be obtained from methanol, which can advantageously be obtained in a simple selective conversion of methane.

Figure 2:
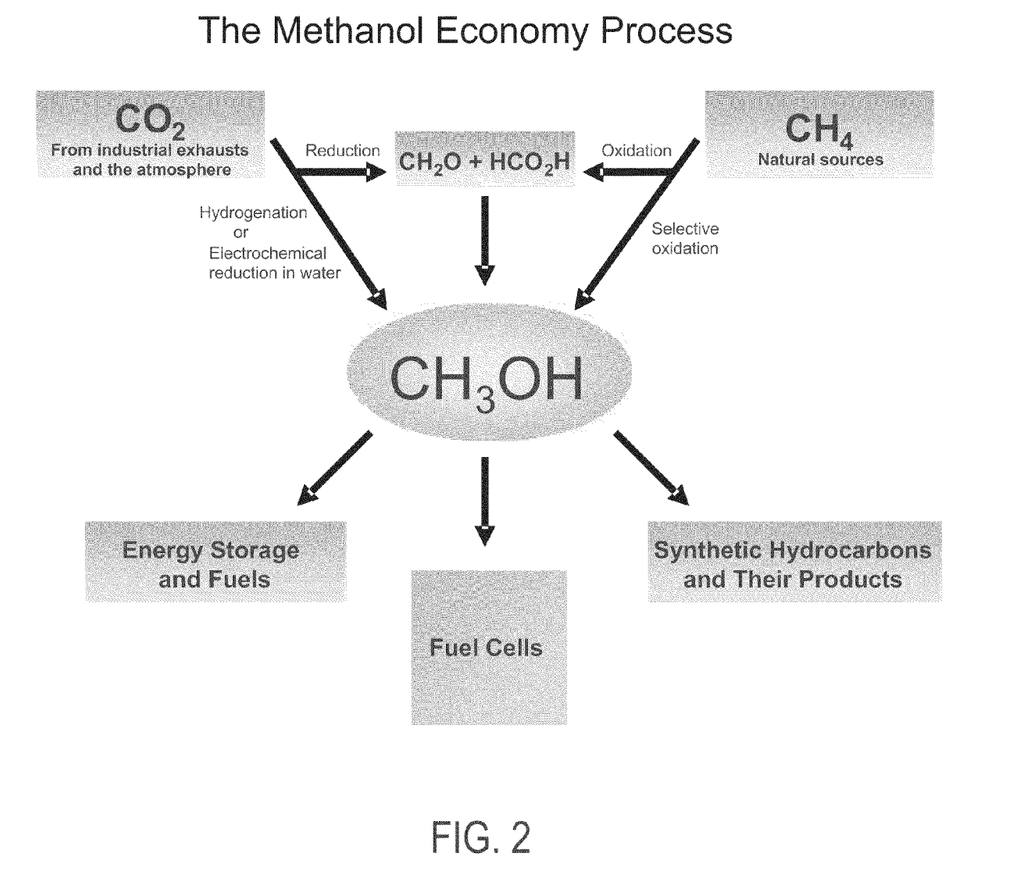
FIG. 2 schematically illustrates the present inventive process termed the METHANOL ECONOMY process by inventor George Olah.

The improved and efficient direct production of methanol from methane (natural gas) according to the present invention also provides the needed raw material for the newly termed METHANOL ECONOMY process, allowing convenient storage of energy in a liquid product that can be used as fuel in the direct oxidation methanol fuel cell and as starting materials for synthetic hydrocarbons for fuel and varied products. METHANOL ECONOMY process is based on efficient direct conversion of natural gas resources to methanol or dimethyl ether, and production of these substances by chemical recycling of carbon dioxide, which can be atmospheric or industrial exhaust gas. The concept of the METHANOL ECONOMY process presents significant advantages and possibilities. In this process, methanol is used as (1) a convenient energy storage medium as itself or in the form of a derived product; (2) a readily transportable and dispensable fuel, including for methanol fuel cells; and (3) a feedstock for synthetic hydrocarbons and their products currently obtained from oil and gas resources, including polymers and even single cell proteins, which can be used for animal feed or human consumption. Methanol and/or dimethyl ether can be produced by the disclosed process using any method of dehydration such as treatment of methanol over a solid acidic catalyst such as Nafion-H or the like. These products are of great practical use as transportation fuels in internal combustion engines or fuel cells. Dimethyl ether can also be used as a substitute for natural gas. Both are also raw materials for olefins (such as ethylene and propylene) and for subsequent production of synthetic hydrocarbons and derived products.

EXAMPLES

The following examples illustrate but not limit the utility of the present process. They are based on the use of known suitable or modified chemical reactions that are applied to the processes of the invention.

Example 1

A gaseous mixture of methane (20 mol %), $O_2$ (10 mol %), diluted with nitrogen, was passed over preheated $SiO_2$ at 650° C. in a quartz tube continuous flow reactor to obtain 17% of formaldehyde in a single passover. The conversion of methane was 30%. Similar reactions over other oxide and mixed oxide catalysts are expected to provide yields of formaldehyde in the range of 10-20% with about 20 to 50% methane conversion. Unreacted methane is recycled. Smaller amounts of CO as well as $CO_2$ that are produced can be used in the additional preparation of methanol. Air can be substituted for oxygen in the oxidation step.

In a subsequent second step, the product mixture formed in the first step without any separation of the reaction products under basic catalytic conditions (CaO, MgO and the like) either under the gas phase flow conditions (100-180° C.) or under batch conditions (at 150° C.) provides methanol and formic acid. The conversion and selectivity in the Cannizzaro reaction is >90%. Methanol and formic acid can be separated or reacted further to produce methyl formate in high yield to be converted to methanol as shown below in Examples 3 and 4.

Example 2

Over a $ZrO_2$ catalyst, the gaseous formaldehyde obtained in Example 1 was reacted at 150° C. to obtain methyl formate in 99% selectivity with 85% conversion. The other aforementioned catalysts are expected to provide similar selectivity and conversions.

Example 3

The methyl formate obtained by the processes of Examples 1 and 2 is catalytically reduced with molecular hydrogen in the gas phase over copper chromite catalysts at atmospheric pressure in the temperature range of 100-230° C. Selectivity to methanol is >90% and methyl formate conversion is about 85 to 90%.

Example 4

A 1:1 mixture of formic acid and formaldehyde obtained from the corresponding products of Example 1 was passed over $WO_3/Al_2O_3$ in a quartz tube reactor at 190° C. Methanol and methyl formate were obtained in overall 40% yield and a 2:1 ratio. The conversion of formic acid was 70%. When the reaction of 1:1 formaldehyde and formic acid ((2 to 10 M solution) in water was carried out at 250° C. in a glass lined reactor, clean conversion gave methanol in 60% yield.

These examples illustrate the general utility of the present process but skilled practitioners can utilize the disclosure and teachings provided herein to generate a wide variety of other chemicals and products as disclosed.

What is claimed is:

1. A method of commercially producing methanol which comprises oxidizing methane in the presence of a catalyst under conditions sufficient to produce an oxidation mixture of methanol and formaldehyde; converting the formaldehyde under conditions sufficient to form methyl formate; and subsequently hydrogenatively converting the methyl formate under conditions sufficient to form methanol; wherein the oxidation mixture is treated without separation of its components to convert the formaldehyde therein to methyl alcohol and formic acid, which are then subsequently converted under conditions sufficient to form methyl formate.

2. The method of claim 1, wherein the oxidation mixture is treated to form methyl alcohol and formic acid which further comprises reacting the formaldehyde with the formic acid produced from the oxidation mixture under conditions sufficient to produce methanol.

3. The method of claim 1, which further comprises subjecting the formaldehyde to catalytic dimerization under conditions sufficient to form the methyl formate.

4. The method of claim 1, wherein the methane is obtained from a source of natural gas, coal gas, or methane hydrates.

5. The method of claim 1, wherein the methane source is oxidized by contact with an oxidizing agent under conditions sufficient to substantially form methanol and formaldehyde.

6. The method of claim 5, wherein the oxidizing agent is molecular oxygen or air.

7. The method of claim 5, wherein the oxidizing agent comprises hydrogen peroxide and the catalyst is an oxide catalyst.

8. The method of claim 7, wherein the oxide catalyst includes single or mixed catalysts based on V, Ti, Ga, Mg, Cu, Mo, Bi, Fe, Mn, Co, Nb, Zr, La or Sn and are optionally provided on a silica or alumina support.

9. The method of claim 1, wherein any unreacted methane is recovered and recycled to be oxidized.

10. The method of claim 1, wherein the methyl formate is converted to methanol by catalytic hydrogenation.

11. The method of claim 1, wherein the methyl formate is converted to methanol by electrochemical reduction.

12. The method of claim 1 which further comprises dehydrating methanol under conditions sufficient to produce dimethyl ether.

13. The method of claim 12 which further comprises heating the dimethyl ether in the presence of an acidic-basic or zeolitic catalysts to form ethylene or propylene.

14. The method of claim 13 which further comprises converting ethylene or propylene either to higher olefins, synthetic hydrocarbons or aromatics and their products for use as feedstocks for chemicals or as transportation fuels.

15. The method of claim 13 which further comprises hydrating ethylene or propylene to form ethanol or propanol.

16. The method of claim 1 which further comprises forming dimethyl carbonate by reaction of the methanol with phosgene or by oxidative carbonylation of the methanol.

* * * * *